(12) United States Patent
Bennett et al.

(10) Patent No.: US 7,256,049 B2
(45) Date of Patent: Aug. 14, 2007

(54) DEVICES AND METHODS FOR SEPARATING PHOSPHOLIPIDS FROM BIOLOGICAL SAMPLES

(75) Inventors: Patrick Kevin Bennett, Salt Lake City, UT (US); Kenneth Charles Van Horne, Denver, CO (US)

(73) Assignee: Tandem Labs, Salt Lake City, UT (US)

( * ) Notice: Subject to any disclaimer, the term of this patent is extended or adjusted under 35 U.S.C. 154(b) by 644 days.

(21) Appl. No.: 10/655,740

(22) Filed: Sep. 4, 2003

(65) Prior Publication Data
US 2005/0054077 A1 Mar. 10, 2005

(51) Int. Cl.
*G01N 33/92* (2006.01)
*G01N 1/18* (2006.01)

(52) U.S. Cl. .............................. 436/71; 436/81; 436/82; 436/177; 436/178; 422/68.1; 422/101; 435/287.1

(58) Field of Classification Search .................. 436/71, 436/73, 81, 82, 174, 177, 178; 422/101, 422/56, 68.1, 69; 435/287.1
See application file for complete search history.

(56) References Cited

U.S. PATENT DOCUMENTS

| | | | | |
|---|---|---|---|---|
| 4,150,045 A * | 4/1979 | Sinha | .......................... | 554/190 |
| 4,257,771 A * | 3/1981 | Yee | .............................. | 436/71 |
| 4,880,574 A * | 11/1989 | Welsh | ......................... | 554/176 |
| 5,231,201 A * | 7/1993 | Welsh et al. | ................. | 554/191 |
| 5,260,028 A | 11/1993 | Astle | | |
| 5,430,170 A * | 7/1995 | Urano et al. | ................. | 558/277 |
| 5,683,953 A | 11/1997 | Mills | | |
| 5,759,549 A * | 6/1998 | Hiltunen et al. | ................ | 554/8 |
| 6,071,410 A | 6/2000 | Nau et al. | | |
| 6,106,721 A | 8/2000 | Bouvier et al. | | |
| 6,177,008 B1 | 1/2001 | Treiber et al. | | |
| 6,248,553 B1 | 6/2001 | Small et al. | | |
| 6,248,911 B1 * | 6/2001 | Canessa et al. | ............. | 554/191 |
| 6,254,780 B1 | 7/2001 | Bouvier et al. | | |
| 6,338,800 B1 | 1/2002 | Kulperger et al. | | |
| 6,346,286 B1 * | 2/2002 | Council et al. | .......... | 426/330.6 |
| 6,350,383 B1 | 2/2002 | Douglas | | |
| 6,417,510 B2 | 7/2002 | Moon et al. | | |
| 6,524,487 B2 | 2/2003 | Kulperger et al. | | |
| 2003/0010722 A1 | 1/2003 | Mills | | |

FOREIGN PATENT DOCUMENTS

WO 99/32885 * 7/1999

OTHER PUBLICATIONS

Brugger, B. et al, Quantitive analysis of biological membrane lipids at the low picomole level by nano-electrospray ionization tandem mass spectrometry, *Proc. Nat'l Acad. Sci USA*, vol. 64, pp. 2339-2344, Mar. 1997, Cell Biology.

Han, Xianlin et al, Electrospray ionization mass spectroscopic analysis of human erthyocyte plasma membrane phospholids, *Proc. Nat'l Acad. Sci. USA*, vol. 91, pp. 10635-10639, Oct. 1994, Chemistry.

Yabusaki, Kenichi, K. et al, Binding of Calcium to Phospatidylcholines as Determined by Proton Magnetic Resonance and Infared Spectroscopy, *Biochemistry*, vol. 14, No. 1, 1975, pp. 162-166.

Sun, Joanne et al, Lanthanide (III)—phosphatidic acid complexes: binding site heterogeneity and phase separation, *Biochimica et Biophysica Acta*, 1024 (1990) pp. 159-166, Elsevier.

Halladay, Helen, N. et al, Optical Properties of TB3+—Phospholipid Complexes and Their Relation to Structure, *Biochemistry*, 1988, 27 2120-2126.

Chrzeszczyk, Adela et al, Evidence for Cooperative Effects in the Bindign of Polyvalent Metal Ions to Pure Phosphatidylcholine Bilayer Vesicle Surfaces, *Biochimica et Biophysica Acta.*, 648, (1981 28-48, Elsevier/North-Holland Biomedical Press.

Petersheim, Matthew et al, Tb3+ and Ca2+ binding to phosphatidylcholine, *Biophys, J.* © Biophysical Society, vol. 56 Sep. 1989, pp. 551-557.

Misiorowski, Ronald L. et al, Competition between Cations and Water for Binding to Phosphatidylcholines in Organic Solvents, *Biochemistry*, vol. 12. No. 5, 1973, pp. 967-975.

Tatulian, Suran A,, Ionization and Ion Binding, Chapter 14 pp. 511-552.

Hauser, Helmut, et al, Ion-Binding to Phospholipids, Interaction of Calcium and Lanthanide Ions with Phospatidylcholine (Lecithin) *Eur. J. Biochem*.58, pp. 133-144 (1975).

Muller, Claudia et al, Ion suppressioin effects in liquid chromatography—electrospary- ionisation transport-region collision induced dissociation mass spectrometry with different serum extradition methods for systematic toxicological analysis with mas spectra libraries, *Journal of Chromatography B*, 773 (2002) pp. 47-52.

King, Richard et al, Mechanistic Investigation of Ionization Suppression in Electrospray Ionization, *J Am Soc Mass Spectrom*, 2000, 11, pp. 942-950.

Murphy, Robert C., Mass Spectrometry of Phospholipids: Tables of Molecular and Product Ions, *Mass Spectrometry of Phospholipids: Tables of Molecular and Product Ions*, Copyright © 2002 pp. 1-71.

Salari, Hassan, Comparitive Study of Solid-Phase and Liquid-Phase Extraction Techniques for Isolation of Phospholipids from Plasma, *Journal of Chromatography*, 419, (1987) pp. 103-111.

Kolarovic, Ladislav, A Comparison of Extraction Methods for the Isolation of Phospholipids from Biological Sources, *Analytical Biochemistry*, 156, pp. 244-250 (1986).

(Continued)

Primary Examiner—Maureen M. Wallenhorst
(74) Attorney, Agent, or Firm—Thorpe North & Western LLP

(57) ABSTRACT

Device and methods for the removal of phospholipids from biological samples are disclosed and described. Removal of phospholipids may be desirable for the analysis of the phospholipids themselves, or to prevent the phospholipids from conflicting with and effectively masking other analytes in the sample for which identification or quantification is sought.

49 Claims, No Drawings

OTHER PUBLICATIONS

Petkovic, Marijana et al, Detection of Individual Phospholipids in Lipid Mixtures by Matrix-Assisted Laser Desorption/Ionization Time-of-Flight Mass Spectrometry: Phosphatidylcholine Prevents the Detection of Further Species, *Analytical Biochemistry*, 289, pp. 202-216 (2001).

Home, Theresa et al, Solid-phase extraction of phospholipids from hemoglobin solutions using Empore styrene divinylbenzen disks, *Journal of Chromatography B*. 695 (1997) pp. 259-267.

Baker, Daniel L. et al, Direct Quantitive Analysis of Lysophosphatidic Acid Molecular Species by Stbale Isotope Dilution Electrospray Ionization Liquid Chromatography-Mass Spectrometry, *Analytical Biochemistry*, 292, pp. 287-295 (2001).

Bonfiglio, Ryan, et al, The Effects of Sample Preparation Methods on the Variability of the Electrospray Ionization Response for Model Drug Compounds, *Rapid Commun. Mass Spectrom*, 13, pp. 1175-1185 (1999).

Harrison, Kathleen A., Negative Ion Electrospray and Tandem Mass Spectrometic Analysis of Platelet Activating Factor (PAF), *J. Mass Spectrum*, 34, pp. 330-335 (1999).

Gibon, Veronique et al, OCL—Oleagineux Corps gras Lipides, *Oleagineux, Corps Gras, Lipides*, vol. 5, Issue 5, Sep.-Oct. 1998.

Castro, Arnold, R. et al, Lipid Removal from Human Serum Samples, *Clin Diagn Lab Immunol*, Mar. 2000; 7 (2): pp. 197-199.

Choi, Bernard, K. et al, Effect of liquid chromatography separation of complex matrices on liquid chromatography-tandem mass spectrometry signal suppression, *Journal of Chromatography*, A. 907 pp. 337-342 (2001).

Halbhuber, K. J. et al, 3 Cerium as capturing agent for orthophosphate and hydrogen peroxide, *Cerium as capturing agent phospohtate and oxidate histoochemicistry*, Published 1994, PCH Publishing, ISBN: 3437115308, pp. 8-12.

\* cited by examiner

DEVICES AND METHODS FOR SEPARATING PHOSPHOLIPIDS FROM BIOLOGICAL SAMPLES

FIELD OF THE INVENTION

The present invention relates to devices and methods for separating phospholipids from biological samples. Accordingly, the present invention relates to the fields of chemistry, biology, medicine, and pharmaceutics.

BACKGROUND

Biological sampling has long been known as a mechanism for obtaining information concerning the physical condition of a subject. A wide variety of sampling techniques and analyses are known, the selection of which may depend on a number of factors, including the specific sample medium, the information sought, and the type of instrumentation to be used in performing the analysis.

As a general matter, most analytical techniques are customized to identify the presence and/or amount of a target substance or constituent in the biological sample. However, in some cases, the presence of certain substances within a sample may interfere with the ability of the analytical technique to obtain and provide such information. In cases where a conflict between sample constituents is identified, attempts are often made to design a sample preparation protocol that removes the problematic substance from the sample to the extent that complete and reliable identification or quantification of the target substance can be achieved.

For example, phospholipids have recently been identified as a potential cause of signal suppression or enhancement, during mass spectroscopic analysis of biological samples for certain target substances. Such suppression or enhancement impairs the accuracy and precision of the resulting data. The chemical configuration of phospholipids includes a hydrophilic polar head group and a hydrophobic tail, which can allow the phospholipid to interact with many different sample constituents. The ability of phospholipids to interact with a variety of substances may be an aspect of their potential to disrupt the assay. Thus, removing the phospholipids from the biological sample prior to mass spectrometric analysis, may allow greater accuracy and reliability of the analytical result obtained.

In some instances, however, removal of phospholipids from a biological sample may be desirable because the phospholipids are themselves the target constituent of interest. In such cases, isolation of the phospholipids from the sample may reduce or eliminate conflicts with certain other constituents and thus improve the reliability of the analysis for the phospholipids.

While removal or separation of phospholipids from a biological sample may be desirable for the above-recited reasons, it is to be noted that such removal should be selective in order to prevent target substances from also being removed along with the phospholipids. Further, when phospholipids are themselves the target substance, the non-selective removal thereof may in some aspects diminish the value of subsequent analytical results obtained.

As a result, methods and devices for separating phospholipids from biological samples, especially for selective separation of phospholipids from biological samples have been sought through research and development efforts.

SUMMARY OF THE INVENTION

Accordingly, the present invention provides methods and devices for removing phospholipids from a biological sample. In one aspect, such a device may include a support, and at least one type of phospholipotropic multivalent cation coupled to the support in a concentration that is sufficient to capture and retain phospholipids from the biological sample.

A variety of phospholipotropic multivalent cations may be used. However, in one aspect, the cation may be a transition metal. In another aspect, the cation may be a lanthanide, for example cerium. In yet another aspect, the cation may be an actinide.

A number of suitable attachment mechanisms may be used to couple the multivalent cation to the support. Examples of such mechanisms include without limitation, ionic bonding, and chelation. However, in one aspect, the attachment may be via an ionic bonding or association. Those of ordinary skill in the art will recognize a wide range of possible chemical groups, or moieties, that may be used to effect the ionic association between the support and the multivalent cation. However, in one detailed aspect of the present invention, the ionic bond may utilize an acid active group. In a more detailed aspect, the acid active group may be selected from the group consisting essentially of sulfonic acid, phosphoric acid, carboxylic acid, acidic silanols, and combinations thereof.

The particular configuration and materials selected for the support may be determined in part by the manner in which the particular device is to be used. For example, in some aspects, the support may be configured as a flat membrane type structure. In other aspects, it may be configured as a matrix suitable to fit into a column, or other structure. Moreover, the materials for the support may vary. For example, in one aspect, the support may include a sorbent material. In another aspect, the support may include an inorganic salt matrix. Examples of suitable sorbent materials are known in the art and include without limitation, alumina, silica, polymers, carbon, zirconium, controlled-pore glass, diatomaceous earth, and combinations thereof. Additionally, the support may include one or more types of functional groups.

The devices of the present invention may take a number of shapes and sizes, and may optionally include various supporting materials, such as external housings and fittings that allow the device to interface with, and/or become attached to, other standard laboratory equipment, such as a syringe body, or in-line column fittings.

The present invention additionally encompasses methods for the fabrication of the devices recited herein. In one aspect, such a method may include the step of coupling at least one type of phospholipotropic multivalent cation with a support in a manner that preserves an affinity of the cation for phospholipids.

Methods of removing phospholipids from biological samples using the devices disclosed herein are also encompassed by the present invention. In one aspect, such a method may include the steps of: a) contacting at least one type of phospholipotropic multivalent cation with the biological sample; b) capturing phospholipids in the sample with the cation; and c) separating the cation and captured phospholipids from the sample. Optionally, such methods may further include the steps of either separating the captured phospholipids from the cation, or separating the cations holding the phospholipids from a support to which the cations are attached, and collecting the phospholipids.

As discussed more fully below, the capturing of the phospholipids according to the methods of the present invention primarily involves ionically associating the phospholipids with the phospholipotropic multivalent cations as described herein. Normally, the separation of the cation and captured phospholipids from the sample will occur by effectively removing the sample from the proximity of the cations, or visa versa. For example, as is well known in the art of chromatography, a sample can be placed in a fluid stream and passed through the cations, which are held stationary, for example by coupling to a support as described herein. In this case, as the fluid stream pushes the sample through, or past the cations, the phospholipids in the sample become captured by the cations while the sample moves on in the fluid stream. Other alternative mechanisms for separating the cations having the captured phospholipids from the biological sample will be recognized by those of ordinary skill in the art.

Desirably, the multivalent cation used will have a higher affinity for phospholipids than for other sample constituents. In some aspects of the invention such selectivity may be important in maximizing the analytical results that can be obtained when attempting to identify and measure analytes with which the phospholipids compete or conflict during a particular type of analysis.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the claims, or may be learned by the practice of the invention.

DETAILED DESCRIPTION

Reference will now be made to the exemplary embodiments that are described as follows, and specific language will be used herein to describe the same. It will nevertheless be understood that no limitation on the scope of the invention is thereby intended. Alterations and further modifications of the inventive features described herein, and additional applications of the principles of the inventions as described herein, which would occur to one skilled in the relevant art and having possession of this disclosure, are to be considered within the scope of the invention.

Definitions

In describing and claiming the present invention, the following terminology will be used in accordance with the definitions set forth below.

The singular forms "a," "an," and, "the" include plural referents unless the context clearly dictates otherwise. Thus, for example, reference to "a sample" includes reference to one or more of such samples, and reference to "the target agent" includes reference to one or more of such target agents.

As used herein, "biological sample" and "sample" may be used interchangeably, and refer to a specimen collected from an organism such as an animal, plant, bacteria, protozoa, fungus, virus, etc. Also, the sample can also be prepared from excretions and wastes produced by an organism, such as feces, urine, sweat, sap, residues, etc. Those of ordinary skill in the art will recognize a variety of ways for preparing such samples for analysis, such as by dilution, or extraction in a liquid, among others.

As used herein, "analyte," "target analyte," "target agent," "target substance," and "constituent" may be used interchangeably, and refer to an agent or substance whose presence, or quantity in a biological sample is sought. Those of ordinary skill in the art are familiar with such terms and their general meaning and use.

As used herein, "support" refers to a material that is capable of having phospholipotropic cations coupled thereto. A support may utilize a number of materials, or have a variety of physical configurations to provide such a capacity. Moreover, specific materials and configurations may be selected and combined in order to provide a support having a desired function and character. Examples of suitable configurations include without limitation, substrates, matrices, membranes, semi-permeable membranes, lattices, backings, bases, beds, molecular sieves, powders, granulates, fibers, etc. Also, the support structure can be rigid, malleable, hard, or soft. Additionally the support can be pre-formed in a shape or free-flowing within a confined space. A support can be in the form of solids, semi-solids, porous solids, gels, hydrogels, fluids, creams, pastes, powders, particulates, salt matrices, microspheres, nanospheres, nanoparticles, emulsions, micelles, reverse micelles, colloids, bilayers, liposomes, microemulsions, films, etc. The support can be heterogeneous and/or homogeneous. Examples of materials that can be used include without limitation, ceramics, hydrophilic substances, hydrophobic substances, composites, crystalline structures, polymers, random polymers, block co-polymers, multimer polymers, linear polymers, branched polymers, segmented polymers, sorbents, inorganic salts, aluminas, silicas, carbons, ziconiums, controlled-pore glass, and diatomaceous earths, and various combinations and compounds thereof. Furthermore, the support micro-structure can be fixed, static, dynamic, mobile, fluid, and/or diffuse. The support can be made of many sections and/or portions that aggregate, flocculate, associate, and/or separate, which can also be segmented into distinct portions with or without boundaries.

As used herein, "phospholipotropic" refers to an agent, substance, or element that has an affinity for phospholipids. In some aspects, the phospholipotropic agent may display a selectivity for phospholipids over other analytes to which the agent may also be attracted. The affinity of the phospholipotropic agent for the phospholipid may be due to a variety of chemical or molecular forces, such as van der Waals, London dispersion, ion-ion, ion-dipole, dipole-dipole, and hydrogen bonding. Further, the phospholipotropic substance and the phospholipid can associate by ionic bonding or chelation.

As used herein, "lanthanide" refers to an element of the periodic table, which can include any of the elements with atomic numbers from 57 to 70. Examples of lanthanides include without limitation lanthanum, cerium, praseodymium, neodymium, etc. In a preferred aspect, the lanthanide may be cerium. Moreover, it is to be understood that as used herein, "lanthanide" also includes compounds and complexes containing a lanthanide element, such as oxides, and other metal salts.

As used herein, "actinide" refers to an element of the periodic table, which can include any of the elements with atomic numbers from 89 to 103. Examples of actinides include without limitation actinium, thorium, protactinium, etc. Moreover, it is to be understood that as used herein, "actinide" also includes compounds and complexes containing an actinide element, such as oxides and other metal salts.

As used herein, "multivalent" refers to an atom or molecule having a valence greater than one.

As used herein, "matrix" refers to a medium or surrounding substance within which something else originates, develops, or is contained, captured, or retained. Also, a matrix can be rigid, malleable, hard, or soft. Additionally, a matrix can be pre-formed in a fixed shape or configuration, or can be free-flowing within a space.

As used herein, "sorbent" refers to composition and/or material that can take up and hold another substance, as by absorption or adsorption. Also, a sorbent can be rigid, malleable, hard, or soft. Additionally a sorbent can be pre-formed in a fixed shape or free-flowing within a space. A variety of sorbent materials are known to those of ordinary skill in the art, which can be used as a support material in the devices of the present invention.

As used herein, "functional group" refers to an aspect of a molecule or a combination of atoms in a molecule that gives the molecule a characteristic chemical behavior. For example, organic chemistry functional groups are typically submolecular structural motifs, characterized by a specific elemental composition and connectivity, which may confer reactivity upon the molecule that contains them. In one aspect, a functional group can be an active acid group. Also, a functional group may be substituted onto a carbon in place of hydrogen on an organic molecule. Common functional groups useful in the present invention include without limitation, halides, alcohols, ethers, aldehydes, ketones, esters, acids, including carboxylic acids, sulfuric acids, sulfonic acids, and phosphoric acids, amines, amides, alkanes, alkenes, alkynes, alkyl halides, aromatic hydrocarbons, nitriles, sulfides, phosphates, azos, phosphodiesters, phenyls, pyridyls, isonitriles, isocyanates, isothiocyanates, thioethers, etc.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of 0.01 to 6 should be interpreted to include not only the explicitly recited limits of 0.01 and 6, but also to include individual numbers such as 0.3, 0.6, 2.0, 2.3, 3.7, 5.4, and sub-ranges such as 0.2-2.3, 1.3-3.9, 2.9-5.1, etc. This interpretation should apply regardless of the breadth of the range or the characteristic being described, and should apply to ranges having both upper and lower numerical values, as well as open-ended ranges reciting only one numerical value.

The Invention

The present invention encompasses methods and devices for removing phospholipids from biological samples. Removal of phospholipids from a biological sample has been discovered to be advantageous for a number of reasons as alluded to above. For example, in many cases, phospholipids may conflict with analytes sought for identification or quantification in the biological sample, or otherwise influence the analytical process. When this happens, the phospholipids may effectively mask the desired analytes and prevent accurate identification or quantification thereof. Additionally, in some cases, the phospholipids may be themselves desired for analysis. Accordingly, removal of the phospholipids from the biological sample is desirable to improve testing accuracy by reducing the possibility of interference from other conflicting analytes.

As a general matter, the methods for removing phospholipids from a biological sample in accordance with the present invention include the steps of: a) contacting at least one type of phospholipotropic multivalent cation with the biological sample; b) capturing phospholipids in the sample with the cation; and c) separating the cation and captured phospholipids from the sample. A number of devices may be used to accomplish such a method. However, such devices will generally include a support, and at least one type of phospholipotropic multivalent cation coupled to the support in a concentration that is sufficient to capture and retain phospholipids from the biological sample.

Those of ordinary skill in the art will recognize a variety of ways in which the phospholipotropic multivalent cation may be brought into contact with the biological sample, and then separated therefrom. Generally speaking, contact may be made by passing the sample past the cations, or visa versa. For example, in one aspect, the sample may be placed in a fluid stream which flows past phospholipotropic multivalent cations that are held stationary on a support. As the sample flows past the cations, the phospholipids become captured by the cations and remain in place while the rest of the sample is driven onward by the flow of the fluid stream.

In another aspect, the sample may be placed in a device that is capable of expelling the sample with an amount of force, such as a syringe. The cations are then coupled to a support that is placed at an opening of the device, and when the sample is expelled from the device it passes past the cations. The phospholipids become captured by the cations, and the remaining portion of the sample moves forward by the expulsion action of the device.

In yet another aspect, the cations may be placed in a solution containing the sample. The sample may be agitated, or otherwise manipulated so that the cations come into contact with, and capture, the phospholipids. The cations with the attached phospholipids are then removed from the solution, leaving the remainder of the sample by itself. Those of ordinary skill in the art will recognize a variety of mechanisms for removing the cations from the solution.

Once the captured phospholipids and cations have been separated from the biological sample, the phospholipids may be separated from the cations and collected. A number of techniques may be used for separating the phospholipids from the cations, such as by contacting the phospholipids with a solution that is sufficient to release the phospholipids from the cations. For example, the phospholipids may be contacted with substances that are capable of ionically out-competing the multivalent cations, or otherwise forming a stronger bond, or association with the phospholipids than the multivalent cations. Those of ordinary skill in the art will recognize a number of possible chemistries that may either have a higher affinity for the phospholipid than the multivalent cation, or reduce the affinity of the cation for the phospholipid. Examples of such competing substances include without limitation, chelating agents, and solvents, such as phosphoric acid, sulfuric acid, hydrochloric acid, hydrofluoric acid, oxalic acid, and other strong organic and inorganic, or mineral acids. Additionally, solvents having strong bases can remove the phospholipids from the cations, such as sodium hydroxide, potassium hydroxide, and ammonium hydroxide. Examples of chelating agents include without limitation, EDTA, IMDA, and NTA, among other chelating organics.

Alternatively, in some aspects of the invention, the phospholipids may remain captured by the multivalent cations, and the cations may be uncoupled from a support to which they are attached. In this manner, it may be possible to further utilize the multivalent nature of the cation, for example, by attaching other chemical entities thereto which may help in quantitative or qualitative analysis, such as fluorescent, phosphorescent, and radioactive elements. A number of techniques may be used to remove cations from a support to which they are coupled. Such techniques will depend in large measure on the type of mechanism holding the cation to the support, the materials of the support, etc. Those of ordinary skill in the art will readily be able to determine various ways of disconnecting a given cation from a given support. For example, if a strong acid group, such as a sulfonic acid, is used to couple the cation to the support, a solution of sulfuric or another strong inorganic or organic acid may be brought into contact with the cation, thus releasing it from the support.

The mechanism for capturing the phospholipids in the biological sample will generally occur by an ionic association, or bond that is formed between the phospholipids and the multivalent cation. In one preferred aspect, the interaction may be an ionic one between a highly oxophilic cation and the organo-phosphate group on the phospholipids. However, in some aspects, additional chemical or molecular forces, such as van der Waals, London dispersion, ion-ion, ion-dipole, dipole-dipole, chelation, and hydrogen bonding forces may provide an affinity for the phospholipids, and aid in the capture thereof from the biological sample. As will be appreciated by one of ordinary skill in the art, the exact number and type of forces will be determined according to the specific multivalent cation, or cation compounds that are used, along with any additional phospholipotropic moieties present.

As noted above, the devices of the present invention that may be used to carry out the methods recited herein will generally include a support, and at least one type of phospholipotropic multivalent cation coupled to the support in a concentration that is sufficient to capture and retain phospholipids from the biological sample. The specific support configuration and material may be selected by one of ordinary skill in the art to provide a device with specific characteristics or operational parameters.

For example, in some aspects, the support may be configured as a flat membrane type structure. Such a flat configuration may be desirable for the high surface area that it presents, and its convenience in allowing a sample to pass along or through it. Further, because of the structural integrity of such a membrane, it may be used in an open or semi-open environment.

In other aspects, the support may be configured as a matrix suitable to fit into a column, or other structure. Such configurations may be especially desirable for use with an apparatus that employs a continuous fluid stream into which the sample is placed. In one aspect, such a matrix may be a single connected structure. In another aspect, such a matrix may be modular or segmented. In yet another aspect, such a matrix may be particulate. For example, a powdered form of the below recited materials may be packed into a column body, cylinder, or other housing that is suitable for holding the particles of powder together while a sample is passed therethrough. In another aspect, the support may be configured in a bulk format suitable for direct addition to the biological sample. Those of ordinary skill in the art will readily recognize a wide variety of other possible configurations that may be suitable for the support of the present invention.

The support used in the devices of the present invention may be made from a variety of materials. Those of ordinary skill in the art will be familiar with many materials that are known for use in somewhat similar devices, such as chromatography columns and filters. One broad class of such materials is sorbents. Examples of specific sorbents include without limitation, alumina, silica, polymers, carbon, zirconium, controlled-pore glass, diatomaceous earth, and combinations thereof. Examples of other classes of materials that may be used include without limitation, fibers made of glass, cellulose, organic polymers, quartz, silica, metals or other materials without limitation. In addition, it is to be noted that in some aspects, the support may be made from an inorganic salt matrix. In such a case, the salt component, or accompanying element of a phospholipotropic multivalent cation compound or complex may act as the support for the cation. For example in the compound cerium oxalate, the oxalate component may act as the support for the cerium which is the multivalent cation.

The support used in the present invention may additionally include one or more types of functional groups, or one or more instances of a single functional group. Such functional groups may be used for the purposes of coupling the multivalent cations to the support, or for a variety of other reasons, such as providing specific patterns of spacing, etc. so as to provide the support with a specific anatomy. Examples of such functional groups may include without limitation, ionic or ionizable groups, chelating groups, hydrogen donating or accepting groups, pi-bonding groups, etc. Optionally, the functional groups may include an active acid group. Examples of useful acid groups include without limitation, sulfonic, phosphoric, phosphonic, carboxylic and other organic acids, dicarboxylic acids, acidic silanols and acidic zirconia groups. In one aspect, the acid group may be a sulfonic acid. In another aspect, the acid may be a phosphoric acid. In yet another aspect, the acid may be an acidic silanols.

The phospholipotropic multivalent cation used in the present invention may be coupled to the support using a variety of chemical mechanisms that suitably retain the cations on the support. Examples of such mechanisms include without limitation, molecular forces such as van der Waals, London dispersion, ion-ion, and ion-dipole interactions. Additional mechanisms include ionic bonding, covalent bonding, and chelation. Further, the cation can be directly coupled to the support, or indirectly through functional groups, linking groups, and/or spacer groups. Such functional groups, linkers and/or spacers are well known in the art to one of ordinary skill and can include active acid groups as recited above, various cross-linked and linear polymers, short and long chain saturated or unsaturated aliphatics, etc. Accordingly, the linker and/or spacer can be of nearly any length required in order to allow the cation to retain its affinity for phospholipids. In one aspect, the cation may be coupled to the support with an ionic bond. In another aspect, the ionic bond may utilize an acid active group, such as those used in connection with the functional groups recited above.

For the purposes of allowing the cations to become detached from the support after the phospholipids have been captured, as recited above, the functional group, including linkers and spacers can be configured to decouple or otherwise lose their integrity upon application of the appropriate chemistry. Such decoupling can be achieved by contacting the linker and/or spacer with a solvent containing a substance that may induce the linker and/or spacer to breakdown, and allow the cation to disassociate from the support. For example, in one aspect, the cation can be ionically coupled to a linker that is hydrogen bonded with the support. In another aspect, the cation can be chelated to as pacer that is covalently bound to the support. In yet another aspect, the cation can be ionically coupled to a spacer that is covalently bound to the support. In an additional aspect, the cation can be ionically coupled to a spacer that is ionically coupled with the support.

A wide variety of substances, many of which will be recognized by those of ordinary skill in the art may be phospholipotropic. However, in one aspect, the phospholipotropic agent may be a multivalent cation. Transition metals may be one source of acceptable cations. For example, copper, iron, nickel, and cobalt all may be used. Other subclasses of transition metals that are particularly suitable include actinides and lanthanides. Examples of suitable actinides include without limitation, actinium, thorium, protactinium, uranium, neptunium, plutonium, americium, curium, berkelium, californium, einsteinium, fermium, mendelevium, nobelium, and lawrencium. Additionally, examples of suitable lanthanides include without limitation, cerium, praseodymium, neodymium, promethium, samarium, europium, gadolinium, terbium, dysprosium, holmium, erbium, thulium, ytterbium, and lutetium. However, in a preferred embodiment of the present invention, the multivalent cation is cerium.

It is to be noted that not only may such multivalent cations be used, but also complexes thereof for the purpose of capturing phospholipids from a biological sample. To this end, various salts, such as lanthanide chlorides, fluorides, oxides, oxalates, citrates, acetates, etc., and complexes such as organo-lanthanides may be used. In one preferred aspect of the invention, the multivalent cation-containing salt may be cerium oxalate.

In one aspect of the present invention, the multivalent cation may have a higher affinity for phospholipids than for other constituents of the biological sample. Such selectivity may be important when analytes of interest exhibit different chemical or physical properties than certain phospholipids. Examples of such analytes include without limitation compounds lacking highly oxygenated functional groups, for example many basic pharmaceutical compounds. Without wishing to be bound by theory, it is speculated that the selectivity shown by certain multivalent cations for phospholipids may be due at least in part to the strongly oxophilic character of the multivalent cations and their selective affinity for the phosphate groups on the phospholipids. Further, as mentioned above, the specific configuration of the support to which the cation is bound may additionally enhance or induce, such selectivity.

As previously noted, in some aspects, the devices of the present invention may include a containment structure, such as an external housing within which the support and phospholipotropic multivalent cation are contained. Such a housing is especially useful when the support is particulate, granular, or free-flowing in nature. However, those of ordinary skill in the art will recognize that such supporting structures may be used to improve the functionality and ease of handling the support and cations regardless of the particular form or configuration they utilize. Specific materials and configurations for the housing or other supporting structure which can be suitably used with the present invention by allowing entry and exit of a biological samples will be readily recognized by those of ordinary skill in the art, and may be selected and employed as required by a number of variables, including the type of samples being analyzed, the mode or mechanism of analysis, the particular shape, form, or physical state of the support and multivalent cations, etc.

The present invention additionally encompasses methods of making a device for removing phospholipids from a biological sample. In some aspects, such a method may include the step of coupling at least one type of phospholipotropic multivalent cation as recited herein, with a support as recited herein, in a manner that preserves an affinity of the cation for phospholipids. Those of ordinary skill in the art will recognize that a variety of coupling mechanisms as recited herein may be suitable to allow the cation to retain its affinity for phospholipids, and that such mechanisms may be selected depending on a variety of factors, including the specific cation to be used. Furthermore, those of ordinary skill in the art will be able to determine optimal coupling mechanisms for a given cation through routine experimentation.

The following example sets are illustrative of particular embodiments and devices and methods in accordance with the present invention. Such examples are provided solely to convey a greater understanding of the present invention to those of ordinary skill in the art, and no limitations thereon are intended, or to be inferred thereby.

EXAMPLES

The following Examples 1-10 are illustrative of different sorbent chemistries utilizing a phospholipotropic multivalent cation for phospholipid capture, and their preparation.

Example 1

Cerium on a phenylsulfonic acid-modified silica—a commercial 50 mg column containing a silica-based phenylsulfonic acid sorbent ("Cerex", Baldwin Park, Calif.) was treated with 2 milliliters of methanol, 2 milliliters of water, 2 milliliters of saturated cerium acetate solution in water, 2 milliliters of water, and 2 milliliters of methanol.

Example 2

Cerium on a phenylsulfonic acid-modified polymer—a commercial 50 mg column containing a polymer-based phenylsulfonic acid sorbent ("Cerex", Baldwin Park, Calif.) was treated with 2 milliliters of methanol, 2 milliliters of water, 2 milliliters of saturated cerium acetate solution in water, 2 milliliters of water, and 2 milliliters of methanol.

Example 3

Cerium on a propylsulfonic acid-modified silica—a commercial 50 mg column containing a silica-based propylsulfonic acid sorbent ("Cerex", Baldwin Park, Calif.) was treated with 2 milliliters of methanol, 2 milliliters of water, 2 milliliters of saturated cerium acetate solution in water, 2 milliliters of water, and 2 milliliters of methanol.

Example 4

Cerium on a propylcarboxylic acid-modified silica—a commercial 50 mg column containing a silica-based propylcarboxylic acid sorbent ("Cerex", Baldwin Park, Calif.) was treated with 2 milliliters of methanol, 2 milliliters of water, 2 milliliters of saturated cerium acetate solution in water, 2 milliliters of water, and 2 milliliters of methanol.

Example 5

Cerium on a propylsulfonic acid-modified silica—a commercial 50 mg column containing a silica-based propylsul fonic acid sorbent ("Cerex", Baldwin Park, Calif.) was treated with 2 milliliters of methanol, 2 milliliters of water, 2 milliliters of saturated cerium chloride solution in water, 2 milliliters of water, and 2 milliliters of methanol.

Example 6

Cerium on an ethyl-modified silica (active silanols on the sorbent are the suspected acidic groups binding the cerium cation)—a commercial 50 mg column containing a silica-based ethyl sorbent ("Cerex", Baldwin Park, Calif.) was treated with 2 milliliters of methanol, 2 milliliters of water, 2 milliliters of saturated cerium acetate solution in water, 2 milliliters of water, and 2 milliliters of methanol.

Example 7

Cerium on a triamine tetraacetate-modified silica—a disposable syringe-barrel column was packed with 50 mg of a triamine tetraacetate-modified silica (Silicycle, Quebec, QC, Canada)". This packed column was treated with 2 milliliters of methanol, 2 milliliters of water, 2 milliliters of saturated cerium acetate solution in water, 2 milliliters of water, and 2 milliliters of methanol.

Example 8

Cerium(III) oxalate hydrate, 99.9% (Aldrich Chemical Co., Milwaukee, Wis.) was used without further treatment or preparation.

Example 9

Lanthanum carbonate hydrate, 99.9% (Aldrich Chemical Co. Milwaukee, Wis.) was used without further treatment or preparation.

Example 10

Cerium (III) citrate was prepared as follows—3.726 grams of cerium (III) chloride heptahydrate in 30 milliliters of water was added to 2.941 grams of sodium citrate dihydrate in 30 milliliters of water. A white precipitate formed and was centrifuged out at 3500 RPM for 5 minutes. The supernatant was poured off. The precipitate was then washed 5 times (to remove dissolved sodium chloride) with 30 milliliters of water by (for each wash) a) addition of water to the precipitate, b) vortex mixing for 2 minutes, and c) centrifugation at 3500 RPM for 5 minutes. The precipitate was then washed in a similar manner 3 times (to remove residual water) with 30 milliliters of methanol (for each wash).

The following Examples 11-15 illustrative of different device formats utilizing the sorbent materials from Examples 1-10 above.

Example 11

A measured amount of the sorbent was added in bulk to the respective sample, vortexed, and the sorbent removed by filtration.

Example 12

A measured amount of the sorbent was added in bulk to the respective sample, vortexed, and the sorbent removed by centrifugation followed by pouring off the supernatant.

Example 13

A disposable extraction column containing the phospholipotropic multivalent cation sorbent was prepared as described in Examples 1-6 above, by starting with a pre-packed commercial column, and modifying the pre-packed column sorbent via treatment with a protocol designed to capture the phospholipotropic multivalent cation onto the pre-packed sorbent.

Example 14

A bulk sorbent was prepared as described in Examples 8-10 above, then the bulk sorbent was packed into a disposable syringe barrel column, between two porous frits designed to contain the sorbent yet allow liquid flow through the column.

Example 15

A column was prepared as described in Example 14 above, but an additional layer of sodium sulfate and an additional frit was placed above the sorbent bed to facilitate water removal from an applied sample.

The following Examples 16-20 are illustrative of different sample treatment methods utilizing the device formats from Examples 11-15 above, and utilizing the sorbents from Examples 1-10 above.

Example 16

Columns containing sorbents treated with a phospholipotropic multivalent cation, and sorbents without such treatment were prepared as follows:

a. A disposable column (see Example 13 above) was used, containing 50 mg of the sorbent from Example 4 above ("CeCBA").

b. A second column was used, containing the same pre-packed sorbent as in step "a." above, but this sorbent was not treated with cerium acetate (referred to as "CBA"). Prior to sample application (step "c." below), this column and the column from step "a." above were treated with 2 milliliters of methanol.

c. A standard Bligh-Dyer extraction of lipids from EDTA human plasma was performed. The lipid fraction from this extraction (containing naturally-occurring phospholipids and lysophospholipids, well-known by those experienced in the art) was dried and reconstituted in an equal volume of methanol (sample "STD"). 200 microliters of this methanol sample were further processed separately through the "CeCBA" column (sample "CeCBA"), and a separate 200 microliters was processed through the "CBA" column (sample "CBA"). 10 microliters of each of these samples was analyzed by positive ion ESI-LC/MS. Two parent ions were monitored, representing two of the major lysophospholipids present in human plasma: 496.0 and 524.0. Values under the parent ions in Table I are raw area counts for the respective chromatographic peaks.

TABLE I

| Sample | 496.0 | % | 524.0 | % |
|---|---|---|---|---|
| STD | 2.4E+04 | 100% | 1.9E+04 | 100% |
| CBA | 3.2E+04 | 133% | 2.0E+04 | 105% |
| CeCBA | 1.5E+03 | 6% | 7.0E+02 | 4% |

As can be seen from the results in Table 1, the sample processed through the untreated "CBA" column shows essentially no phospholipid capture as compared to the sample "STD", while the sample processed through the cerium acetate-treated "CeCBA" column shows >90% lysophospholipid capture.

The following example illustrates a comparison between target analyte and phospholipid recoveries from spiked plasma extracted by protein precipitation, as compared to similar samples processed after protein precipitation through a phospholipotropic multivalent cation-containing sorbent. The example also illustrates extraction selectivity for the phospholipids as compared to the target analytes.

Example 17 a. A stock solution was prepared to contain the following target analytes in methanol: triprolidine, quinidine, ketoconazole and reserpine. Levels of each analyte were adjusted so as to each give a similar signal level by ESI-LC/MS/MS with a 20 microliter injection in positive ionization mode using the following four respective transitions: 279.2→208.0; 325.2→81.2; 531.2→82.0; 609.6→194.8.

b. The following five transitions were monitored by ESI-LC/MS/MS as representative of extract phospholipid content: 496.4→184.0; 524.4→184.0; 704.5→184.0; 758.6→184.0; 806.5→184.0.

c. (Experiment performed in triplicate, and recoveries averaged.) 200 microliters of stock solution (step "a." above) was added to each of two tubes and brought to dryness. To each tube was then added 400 microliters of plasma, and the tubes were vortexed for two minutes. An additional 1.5 milliliters of acetonitrile was then added to each tube, to precipitate proteins. The samples were vortexed, centrifuged, decanted, and the supernatant brought to dryness. To one tube was added 400 microliters of methanol ("PPTA"), and to the other was added 200 microliters of methanol ("PPTB1"). The tubes were vortexed again.

d. Extract "PPTB 1" was further passed through a column (see Example 13 above) containing a 100 mg bed of a phospholipotropic multivalent cation-containing sorbent (see Example 3 above) and collected (Fraction 1). The column was washed with an additional 200 milliliters of 1:1::water:methanol, and the wash combined with Fraction 1, to give sample "PPTB".

e. 10 microliter injections of samples "PPTA" and "PPTB" were analyzed for recoveries of phospholipids and target analytes via positive ion MRM ESI-LC/MS/MS, using the transitions listed above in steps "a." and "b." Recoveries for components of sample "PPTB" in Table II below are shown as percentages of "PPTA" component recoveries, to illustrate the effect of the extraction column. Values under the phospholipid parent ions and target analyte names in Table II below are raw area counts for the respective chromatographic peaks.

TABLE II

| Sample | Tripro | | Quin | | Keto | | Reserp | |
|---|---|---|---|---|---|---|---|---|
| PPTA | 1.12E+05 | 100.0% | 1.45E+05 | 100.0% | 9.12E+04 | 100.0% | 1.19E+05 | 100.0% |
| PPTB | 9.89E+04 | 87.9% | 9.02E+04 | 62.2% | 7.94E+04 | 87.2% | 8.58E+04 | 72.2% |

| | 496 | | 524 | | 704 | | 758 | | 806 | |
|---|---|---|---|---|---|---|---|---|---|---|
| PPTA | 3.05E+06 | 100.0% | 1.23E+06 | 100.0% | 1.07E+05 | 100.0% | 3.45E+06 | 100.0% | 5.99E+05 | 100.0% |
| PPTB | 1.32E+04 | 0.4% | 4.73E+02 | 0.0% | 2.19E+03 | 2.0% | 5.03E+04 | 1.5% | 5.19E+03 | 0.9% |

As illustrated in Table II above, the extraction column used removed >97% of the monitored phospholipids as compared to protein precipitation alone. Some removal of target analytes was also exhibited; however, the amounts were much lower (<40%), indicating selectivity of the extraction mechanism for phospholipids.

The following example illustrates a comparison between target analyte and phospholipid recoveries from spiked plasma extracted by liquid/liquid extraction with methyl t-butyl ether ("MTBE extraction"), as compared to similar samples processed after MTBE extraction through a phospholipotropic multivalent cation-containing sorbent.

Example 18 a. A stock solution was prepared to contain the following analytes in methanol: triprolidine, quinidine, ketoconazole and reserpine. Levels of each analyte were adjusted so as to each give a similar signal level by ESI-LC/MS with a 20 microliter injection in positive ionization mode using the following respective transitions: 279.2→208.0; 325.2→81.2; 531.2→82.0; 609.6→194.8.

b. The following five transitions were monitored by ESI-LC/MS/MS as representative of extract phospholipid content: 496.4→184.0; 524.4→184.0; 704.5→184.0; 758.6→184.0; 806.5→184.0.

c. (Experiment performed in triplicate, and recoveries averaged.) 200 microliters of stock solution (step "a." above) was added to each of two tubes and brought to dryness. To each tube was then added 400 microliters of plasma, and the tubes were vortexed for two minutes. Then 4 milliliters of MTBE was added, the samples were vortex mixed, the MTBE removed via freeze-pour technique, and the MTBE supernatant brought to dryness. To one tube was added 400 microliters of methanol ("LLA"), and to the other was added 200 microliters of methanol ("LLB1"). The tubes were vortexed again.

d. Extract "LLB1" was further passed through a column (see Example 13 above) containing a 100 mg bed of a phospholipotropic multivalent cation-containing sorbent (see Example 3 above) and collected (Fraction 1). The column was washed with an additional 200 millilliters of 1:1::water:methanol, and the wash combined with Fraction 1, to give sample "LLB".

e. 10 microliter injections of samples "LLA" and "LLB" were analyzed for recoveries of phospholipids and target analytes via positive ion MRM ESI-LC/MS/MS, using the transitions listed above in steps "a." and "b." Recoveries for components of sample "LLB" in Table III below are shown as percentages of "LLA" component recoveries, to illustrate the effect of the extraction column. Values under the phospholipid parent ions and target analyte names in Table III below are raw area counts for the respective chromatographic peaks.

content: 496.4→184.0; 524.4→184.0; 704.5→184.0; 758.6→184.0; 806.5→184.0.

c. (Experiment performed in triplicate, and recoveries averaged.) 200 microliters of stock solution (step "a." above) was added to each of two tubes and brought to dryness. To each tube was then added 400 microliters of plasma, and the tubes were vortexed for two minutes. An additional 1.5 milliliters of acetonitrile was then added to each tube, to precipitate proteins. The samples were vortexed, centrifuged, decanted, and the supernatant brought to dryness. To one tube was added 400 microliters of methanol

TABLE III

| Sample | Tripro | | Quin | | Keto | | Reserp | |
|---|---|---|---|---|---|---|---|---|
| LL A | 1.32E+05 | 100.0% | 1.26E+05 | 100.0% | 8.30E+04 | 100.0% | 1.17E+05 | 100.0% |
| LL B | 4.86E+04 | 36.7% | 2.13E+04 | 16.9% | 7.69E+04 | 92.7% | 3.35E+04 | 28.7% |

| | 496 | | 524 | | 704 | | 758 | | 806 | |
|---|---|---|---|---|---|---|---|---|---|---|
| LL A | 2.97E+05 | 100.0% | 1.55E+05 | 100.0% | 1.47E+05 | 100.0% | 2.32E+06 | 100.0% | 2.75E+05 | 100.0% |
| LL B | 6.54E+02 | 0.2% | 1.00E+02 | 0.1% | 1.17E+03 | 0.8% | 3.01E+04 | 1.3% | 2.93E+03 | 1.1% |

As illustrated in Table III above, the column used for extraction removed >98% of the monitored phospholipids. Some removal of target analytes was also exhibited; however, the amounts were much lower than those for the phospholipids (~7-83%), indicating selectivity of the extraction mechanism for phospholipids.

The following example illustrates a comparison between target analyte and phospholipid recoveries from spiked plasma extracted by protein precipitation, as compared to similar samples processed after protein precipitation through a phospholipotropic multivalent cation-containing sorbent. The example also illustrates extraction selectivity for the phospholipids as compared to the target analytes. Further, the addition of formic acid to the column wash improves recovery of target analytes without affecting removal of phospholipids, thus enhancing selectivity further.

("PPTA"), and to the other was added 200 microliters of methanol ("PPTB1"). The tubes were vortexed again.

d. Extract "PPTB1" was further passed through a column (see Example 13 above) containing a 100 mg bed of a phospholipotropic multivalent cation-containing sorbent (see Example 3 above) and collected (Fraction 1). The column was washed with an additional 200 millilliters of 1:1::water:methanol containing 1% formic acid, and the wash combined with Fraction 1, to give sample "PPTB".

e. 10 microliter injections of samples "PPTA" and "PPTB" were analyzed for recoveries of phospholipids and target analytes via positive ion MRM ESI-LC/MS/MS, using the transitions listed above in steps "a." and "b." Recoveries for components of sample "PPTB" in Table II below are shown as percentages of "PPTA" component recoveries, to illustrate the effect of the extraction column. Values under the phospholipid parent ions and target analyte names in Table IV below are raw area counts for the respective chromatographic peaks.

TABLE IV

| Sample | Tripro | | Quin | | Keto | |
|---|---|---|---|---|---|---|
| PPTA | 8.49E+05 | | 6.59E+05 | | 6.25E+05 | |
| PPTB | 7.15E+05 | 84.2% | 5.66E+05 | 86.0% | 5.77E+05 | 92.4% |

| | 496 | | 524 | | 704 | | 758 | | 806 | |
|---|---|---|---|---|---|---|---|---|---|---|
| PPTA | 5.30E+06 | | 4.54E+06 | | 8.81E+05 | | 2.31E+07 | | 3.93E+06 | |
| PPTB | 1.57E+04 | 0.3% | 4.54E+03 | 0.1% | 9.84E+03 | 1.1% | 1.82E+05 | 0.8% | 2.13E+04 | 0.5% |

Example 19 a. A stock solution was prepared to contain the following target analytes in methanol: triprolidine, quinidine, and ketoconazole. Levels of each analyte were adjusted so as to each give a similar signal level by ESI-LC/MS/MS with a 20 microliter injection in positive ionization mode using the following four respective transitions: 279.2→208.0; 325.2→81.2; 531.2→82.0.

b. The following five transitions were monitored by ESI-LC/MS/MS as representative of extract phospholipid As illustrated in Table IV, the extraction column used removed ~99% of the monitored phospholipids as compared to protein precipitation alone. Some removal of target analytes was also exhibited; however, the amounts were much lower (<16%), indicating improved selectivity of the extraction mechanism for phospholipids.

The following example illustrates a comparison between target analyte and phospholipid recoveries from spiked plasma extracted by liquid/liquid extraction with methyl t-butyl ether ("MTBE extraction"), as compared to similar samples processed after MTBE extraction by addition of a bulk phospholipotropic multivalent cation-containing inorganic salt.

Example 20 a. A stock solution was prepared to contain the following analytes in methanol: triprolidine, quinidine, PPT, ketoconazole and reserpine. Levels of each analyte were adjusted so as to each give a similar signal level by ESI-LC/MS/MS with a 20 microliter injection in positive ionization mode using the following respective transitions: 279.2→208.0; 325.2→81.2; 415.2→247.0; 531.2→82.0; 609.6→194.8.

b. The following five transitions were monitored by ESI-LC/MS/MS as representative of extract phospholipid content: 496.4→184.0; 524.4→184.0; 704.5→184.0; 758.6→184.0; 806.5→184.0.

c. (Experiment performed in triplicate, and recoveries averaged.) 200 microliters of stock solution (step "a." above) was added to each of two tubes and brought to dryness. To each tube was then added 400 microliters of plasma, and the tubes were vortexed for two minutes. Then 2 milliliters of MTBE was added, the samples were vortex mixed for 5 minutes, centrifuged to separate the phases, and the MTBE removed via freeze-pour technique. To one of these was added 100 milligrams of cerium oxalate (see Example 8 above) to give sample "CeOx", and to the other nothing additional was added, to give sample "STD". The tubes were vortexed again for 2 minutes, spun down by centrifugation, the supernatants removed, dried, and reconstituted in 800 microliters of acetone.

d. 10 microliter injections of samples "STD" and "CeOx" were analyzed for recoveries of phospholipids and target analytes via positive ion MRM ESI-LC/MS/MS, using the transitions listed above in steps "a." and "b." Recoveries for components of sample "CeOx" in Table V below are shown as percentages of "STD" component recoveries, to illustrate the effect of the bulk cerium oxalate addition. Values under the phospholipid parent ions and target analyte names in Table V below are raw area counts for the respective chromatographic peaks.

TABLE V

| Sample | Tripro | | Quin | | PPT | | Keto | | Reserp | |
|---|---|---|---|---|---|---|---|---|---|---|
| STD | 1.09E+05 | 100.0% | 8.40E+04 | 100.0% | 1.00E+00 | 100.0% | 1.40E+05 | 100.0% | 9.82E+04 | 100.0% |
| CeOx | 1.10E+05 | 100.6% | 8.54E+04 | 101.7% | 1.00E+00 | 100.0% | 1.43E+05 | 102.5% | 9.57E+04 | 97.5% |
| | 496 | | 524 | | 704 | | 758 | | 806 | |
| STD | 1.26E+04 | 100.0% | 6.26E+03 | 100.0% | 1.01E+05 | 100.0% | 2.32E+06 | 100.0% | 3.00E+05 | 100.0% |
| CeOx | 6.44E+02 | 5.1% | 2.37E+02 | 3.8% | 2.98E+03 | 3.0% | 1.22E+05 | 5.3% | 1.21E+04 | 4.1% |

As illustrated in Table V, the addition of bulk cerium oxalate removed >94% of the monitored phospholipids, while removing <3% of the respective target analytes, illustrating significant selectivity of the extraction mechanism for phospholipids.

It is to be understood that the above-referenced arrangements are only illustrative of certain embodiments of the present invention. Numerous modifications and alternative arrangements can be devised by those of ordinary skill in the art without departing from the spirit and scope of the present invention, such as modifications in size, shape, materials, etc., and the appended claims are intended to cover such modifications and arrangements.

What is claimed is:

1. A device for removing phospholipids from a biological sample, comprising:
   a) a support; and
   b) at least one type of phospholipotropic multivalent cation coupled to the support in a concentration that is sufficient to capture and retain phospholipids from the biological sample said cation including either an actinide, or a lanthanide or a mixture thereof, said lanthanide being selected from the group consisting of: cerium, lanthanum, europium, neodymium, gadolinium, or a mixture thereof.

2. The device of claim 1, wherein the lanthanide is cerium.

3. The device of claim 1, wherein the phospholipotropic multivalent cation is coupled to the support with an attachment selected from the group consisting of an ionic bond, chelation, and combinations thereof.

4. The device of claim 3, wherein the ionic bond utilizes an acid active group.

5. The device of claim 4, wherein the acid active group is selected from the group consisting of sulfonic acid, phosphoric acid, carboxylic acid, acidic silanols acidic zirconia and combinations thereof.

6. The device of claim 1, wherein the support is an inorganic salt matrix.

7. The device of claim 1, wherein the support is a sorbent.

8. The device of claim 1, wherein the support includes a member selected from the group consisting of alumina, silica, polymers, carbon, zirconium, controlled-pore glass, diatomaceous earth, and combinations thereof.

9. The device of claim 8, wherein the support includes a functional group.

10. The device of claim 1, wherein the phospholipotropic multivalent cation retains the phospholipid until the cation is contacted with a solution that is sufficient to release the phospholipid from the cation.

11. The device of claim 1, wherein the phospholipotropic multivalent cation is coupled to the support until the cation is contacted with an agent that is sufficient to release the cation from the support.

12. A method of removing phospholipids from a biological sample, comprising:
   a) contacting at least one type of phospholipotropic multivalent cation selected from the group consisting of lanthanides and actinides, and coupled to a support, with the biological sample;
   b) capturing phospholipids in the sample with the cation by chemically coordinating including chelating or ionically associating the phospholipids with the cation; and
   c) separating the cation and captured phospholipids from the sample.

13. The method of claim 12, further comprising the step of separating the captured phospholipids from the cation.

14. The method of claim 13, further comprising the step of collecting the phospholipids.

15. The method of claim 12, wherein the phospholipotropic multivalent cation is a transition metal.

16. The method of claim 12, wherein the phospholipotropic multivalent cation is a lanthanide.

17. The method of claim 16, wherein the lanthanide is cerium.

18. The method of claim 12, wherein the phospholipotropic multivalent cation is an actinide.

19. The method of claim 12, wherein the phospholipotropic multivalent cation is coupled to a support.

20. The method of claim 19, wherein the support is an inorganic salt matrix.

21. The method of claim 19, wherein the support includes a member selected from the group consisting of alumina, silica, polymers, carbon, zirconium, controlled-pore glass, diatomaceous earth, and combinations thereof.

22. The method of claim 19, further comprising the step of separating the phospholipotropic multivalent cation from the support.

23. A method of making a device for removing phospholipids from a biological sample, comprising:
    coupling at least one type of phospholipotropic multivalent cation with a support by a mechanism selected from the group consisting of ionic bonding, covalent bonding, chemical coordination including chelation, and combinations thereof, in a manner that preserves an affinity of the cation for phospholipids and in concentration that is sufficient to capture and retain phospholipids from the biological sample, said cation including either an actinide, or a lanthanide or a mixture thereof, said lanthanide being selected from the group consisting of: cerium, lanthanum, europium, neodymium, gadolinium, or a mixture thereof.

24. The method of claim 23, wherein the cation is coupled to the support using an acid active group.

25. The method of claim 24, wherein the acid active group is selected from the group consisting of sulfonic acid, phosphoric acid, carboxylic acid, acidic silanol, acidic zirconia, and combinations thereof.

26. The method of claim 23, wherein the lanthanide is cerium.

27. The method of claim 23, wherein the support is an inorganic salt matrix.

28. The method of claim 23, wherein the support includes a member selected from the group consisting of alumina, silica, polymers, carbon, zirconium, controlled-pore glass, diatomaceous earth, and combinations thereof.

29. The method of claim 28, wherein the support includes a functional group.

30. A device for removing phospholipids from a biological sample, comprising:
    a) an inorganic salt matrix support; and
    b) at least one type of phospholipotropic multivalent cation selected from the group consisting of lanthanides and actinides coupled to the inorganic salt matrix support by a mechanism selected from the group consisting of ionic bonding, covalent bonding, chemical coordination including chelation, and combinations thereof, in a concentration that is sufficient to capture and retain phospholipids from the biological sample.

31. The device of claim 30, wherein the phospholipotropic multivalent cation is a transition metal.

32. The device of claim 30, wherein the phospholipotropic multivalent cation is a lanthanide.

33. The device of claim 32, wherein the lanthanide is cerium.

34. The device of claim 30, wherein the phospholipotropic multivalent cation is an actinide.

35. The device of claim 30, wherein the coupling is by an ionic bond.

36. The device of claim 35, wherein the ionic bond utilizes an acid active group.

37. The device of claim 36, wherein the acid active group is selected from the group consisting of sulfonic acid, phosphoric acid, carboxylic acid, acidic silanols acidic zirconia and combinations thereof.

38. The device of claim 30, wherein the phospholipotropic multivalent cation retains the phospholipid until the cation is contacted with a solution that is sufficient to release the phospholipid from the cation.

39. The device of claim 30, wherein the phospholipotropic multivalent cation is coupled to the support until the cation is contacted with an agent that is sufficient to release the cation from the support.

40. A method of removing phospholipids from a biological sample, comprising:
    a) contacting at least one phospholipotropic multivalent cation selected from the group consisting of lanthanides or actinides coupled to a support with the biological sample;
    b) capturing phospholipids in the sample with the cation; and
    c) separating the cation and captured phospholipids from the sample.

41. The method of claim 40, further comprising the step of separating the captured phospholipids from the cation.

42. The method of claim 41, further comprising the step of collecting the phospholipids.

43. The method of claim 40, wherein the capturing includes ionically associating the phospholipids with the phospholipotropic multivalent cation.

44. The method of claim 40, wherein the phospholipotropic multivalent cation is a lanthanide.

45. The method of claim 44, wherein the lanthanide is cerium.

46. The method of claim 40, wherein the phospholipotropic multivalent cation is coupled to a support.

47. The method of claim 46, wherein the support is an inorganic salt matrix.

48. The method of claim 46, wherein the support includes a member selected from the group consisting of alumina, silica, polymers, carbon, zirconium, controlled-pore glass, diatomaceous earth, and combinations thereof.

49. The method of claim 46, further comprising the step of separating the phospholipotropic multivalent cation from the support.

* * * * *